(12) United States Patent
Kawana (10) Patent No.: US 9,435,774 B2
(45) Date of Patent: Sep. 6, 2016

(54) GAS CHROMATOGRAPH APPARATUS

(71) Applicant: SHIMADZU CORPORATION, Kyoto-shi, Kyoto (JP)

(72) Inventor: Shuichi Kawana, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 300 days.

(21) Appl. No.: 13/905,652

(22) Filed: May 30, 2013

(65) Prior Publication Data
US 2014/0352406 A1    Dec. 4, 2014

(51) Int. Cl.
| G01N 30/02 | (2006.01) |
| G01N 30/16 | (2006.01) |
| G01N 30/38 | (2006.01) |
| G01N 30/32 | (2006.01) |

(52) U.S. Cl.
CPC ......... *G01N 30/38* (2013.01); *G01N 2030/324* (2013.01); *G01N 2030/385* (2013.01)

(58) Field of Classification Search
CPC .......... G01N 2030/025; G01N 30/16; G01N 30/7206
See application file for complete search history.

(56) References Cited

U.S. PATENT DOCUMENTS

| 5,044,860 | A | * | 9/1991 | Norem et al. | 414/287 |
| 5,339,673 | A | * | 8/1994 | Nakagawa et al. | 73/23.36 |
| 5,467,635 | A | * | 11/1995 | Nakagawa et al. | 73/23.35 |
| 5,856,616 | A | * | 1/1999 | Maswadeh et al. | 73/23.42 |
| 7,803,635 | B1 | * | 9/2010 | Meece | 436/181 |
| 8,092,744 | B1 | * | 1/2012 | Meece | 422/68.1 |
| 2010/0101304 | A1 | * | 4/2010 | McIntyre et al. | 73/23.37 |
| 2011/0100093 | A1 | * | 5/2011 | Kawana | 73/23.42 |
| 2013/0125620 | A1 | * | 5/2013 | Ovadia | G01N 30/08 73/23.39 |
| 2014/0250978 | A1 | * | 9/2014 | McCauley | 73/23.39 |

FOREIGN PATENT DOCUMENTS

| JP | 60149969 A | * | 8/1985 | G01N 30/72 |
| JP | 04269655 A | * | 9/1992 | G01N 30/02 |
| JP | 2000-304751 A |  | 11/2000 | |
| JP | 2009128305 A | * | 6/2009 | |
| JP | 2011095072 A | * | 5/2011 | |
| JP | 2013044647 A | * | 3/2013 | |
| WO | WO 2015045028 A1 | * | 4/2015 | |

OTHER PUBLICATIONS

Agilent Technologies, Inc. "Agilent Programmable Helium Conservation Module"; Prevent Business Disruptions by Managing Your Helium Usage (Apr. 30, 2013) two pages total.

* cited by examiner

*Primary Examiner* — David A Rogers
(74) *Attorney, Agent, or Firm* — Sughrue Mion, PLLC (57) ABSTRACT

A gas chromatograph having a column which separates respective components contained in a gas sample introduced via a carrier gas over time, wherein an analysis mode and a standby mode can be switched and executed. The gas chromatograph apparatus comprises: a carrier gas flow path, a column protection gas flow path, a flow path switching part provided between the carrier gas flow path and the column protection gas flow path and a column so that only one of the carrier gas or a column protection gas is introduced into the column, and a flow path control part for controlling the flow switching part so as to introduce the carrier gas into the column at the time of the analysis mode and introduce the column protection gas into the column at the time of the standby mode.

6 Claims, 6 Drawing Sheets

(a) Case of a capillary column with a length of 30 m

| GAS TYPE | COLUMN OVEN TEMPERATURE | |
|---|---|---|
| | 40°C | 100°C |
| $H_2$ | 3.96 ml/min | 2.94 ml/min |
| He | 1.78 ml/min | 1.33 ml/min |
| $N_2$ | 1.45 ml/min | 1.97 ml/min |
| Ar | 1.55 ml/min | 1.13 ml/min |

(b) Case of a capillary column with a length of 10 m

| GAS TYPE | COLUMN OVEN TEMPERATURE | |
|---|---|---|
| | 40°C | 100°C |
| $H_2$ | 8.82 ml/min | 11.88 ml/min |
| He | 4 ml/min | 5.34 ml/min |
| $N_2$ | 4.35 ml/min | 5.91 ml/min |
| Ar | 3.38 ml/min | 4.64 ml/min |

FIG. 6

GAS CHROMATOGRAPH APPARATUS

TECHNICAL FIELD

The present invention relates to a gas chromatograph apparatus. More specifically, the present invention relates to control technology for a gas chromatograph apparatus.

BACKGROUND ART

A gas chromatograph apparatus is an apparatus which feeds a gas sample into a column via a carrier gas, separates the respective components in the sample over time inside the column, and detects the components with a detector provided at the column outlet. Since the rates at which the respective components move into the column differ depending on the strengths of the interactions between the respective components in the sample and a stationary phase inside the column, the respective components are separated over time. At this time, the flow rate of the carrier gas is set to a rate within an optimal flow rate range at which the components in the sample can be sufficiently separated and at which peaks with sharp shapes can be obtained. In many gas chromatograph apparatuses, helium gas is used as a carrier gas due to a wide optimum flow rate range and high safety. Although inferior to helium gas from the perspective of safety, hydrogen gas is also sometimes used as a carrier gas due to a wide optimum flow rate range, as in the case of helium gas.

The rates at which the carrier gas or the respective components in the sample move into the column change due to the temperature or the like inside the column. Therefore, analysis cannot be performed accurately until these are stabilized. However, a long amount of time is required from when the power of the apparatus is turned on until the temperature or the like inside the column is stabilized at a prescribed value. Therefore, even if there is a certain amount of time after a given analysis is completed until the next analysis is performed, it is typical to maintain a standby state in which the temperature or the like inside the column is stabilized at a prescribed value in the same manner as at the time of analysis while the power is kept on. The carrier gas is circulated into the column even in the standby state. This is to prevent the stationary phase inside the column from degenerating due to water content or oxygen infiltrating from the outside or, conversely, to prevent the stationary phase from flowing out from the column outlet when the outlet side of the column is in a vacuum state, such as in the case of GC/MS, for example.

In this way, the column of a gas chromatograph apparatus is protected by circulating a carrier gas into the column even in the standby state. However, when the same amount of the carrier gas as at the time of measurement is circulated in the standby state, the running cost becomes high. In order to alleviate this problem, Patent Literature 1, for example, proposes a gas chromatograph apparatus which reduces the flow volume of carrier gas in the standby state.
PATENT LITERATURE 1—Japanese Unexamined Patent Application Publication 2000-304751

When the gas chromatograph apparatus described in Patent Literature 1 is used, the flow volume of the carrier gas in the standby state can be suppressed. However, even if the flow volume is suppressed, the amount of carrier gas consumption becomes large when the standby state continues for a long time. In particular, helium gas, which is used as the carrier gas of many gas chromatograph apparatuses, has become increasingly expensive in recent years, and there is a demand for a scheme to suppress the running cost of the apparatus.

The problem to be solved by the present invention is to provide a gas chromatograph apparatus and a gas chromatograph mass spectrometry apparatus capable of protecting a column at low cost in the standby state.

SUMMARY OF THE INVENTION

The present invention, which was conceived in order to solve the problem described above, is a gas chromatograph apparatus having a column which separates respective components contained in a gas sample introduced via a carrier gas over time, wherein an analysis mode in which an analysis of the gas sample is executed and a standby mode in which an analysis is not executed can be switched and executed, the gas chromatograph apparatus including:

a) a carrier gas flow path for introducing the carrier gas into the column;

b) a column protection gas flow path for introducing a column protection gas separate from the carrier gas into the column;

c) a flow path switching part provided between the carrier gas flow path and the column protection gas flow path and the column so that only one of the carrier gas or the column protection gas is introduced into the column; and d) a flow path control part for introducing the carrier gas into the column at the time of the analysis mode and introducing the column protection gas into the column at the time of the standby mode.

In the gas chromatograph apparatus of the present invention, a gas that is less expensive than the gas used as the carrier gas can be used as the column protection gas. For example, when the carrier gas is helium gas, the column should be protected in the standby mode (standby state) using nitrogen gas, argon gas, hydrogen gas, or the like as the column protection gas. As a result, the column can be protected at a lower cost than in a conventional chromatograph apparatus which protects the column using helium gas in the standby state. When the carrier gas is hydrogen gas, nitrogen gas, argon gas, or the like should be used as the column protection gas.

Further, a gas of the same type as the carrier gas but with a lower purity may also be used as the column protection gas.

The gas chromatograph apparatus of the present invention may include:

e) a flow controller having at least one control mode from among a constant linear velocity mode, a constant flow volume mode, and a constant pressure mode as a mode for controlling a flow state of a gas introduced into the column;

f) a determination part for estimating at least one value of a linear velocity, a flow volume of the column protection gas, and a pressure of the column protection gas when the gas introduced into the column is changed from the carrier gas to the column protection gas without changing the control mode of the flow controller and parameters related to the mode at the time of a transition from the analysis mode to the standby mode and determining whether the estimated value is within a preset range; and g) a change indication part for prompting a user to change the control mode of the flow controller and/or the parameters related to the mode by means of a predetermined method if the determination part determines that the estimated value is not within the range.

When the types of gasses differ, the characteristics such as the viscosity change. Therefore, if the control mode of the flow controller is continued as it is and the parameters related to the mode remain the same even after the gas is switched, the values of parameters controlled with a device of the gas introduction part (gas flow volume, gas pressure, and the like) differ when introducing the carrier gas into the column and when introducing the column protection gas into the column. For example, when switching the gas to be introduced into the column from a gas of high viscosity to a gas of low viscosity while controlling the flow state of the gas in the constant linear velocity mode, it is necessary to reduce the flow volume of the gas circulated into the column. In such a case, the flow volume may drop below the lower limit of the flow rate that can be controlled by the device of the gas introduction part, which may make it impossible to control the flow state of the gas.

Providing the gas chromatograph apparatus of the present invention with the configuration described above makes it possible to prevent situations in which the flow volume or pressure of the gas can no longer be controlled at the time of a transition from the analysis mode to the standby mode.

The gas chromatograph apparatus of the present invention may include:

h) a notification part for notifying a user that the replacement of the column protection gas with the carrier gas has been completed by means of a prescribed method after a prescribed amount of time has passed since the switching performed by the flow path switching part at the time of a transition from the standby mode to the analysis mode.

When transitioning from the standby mode to the analysis mode, a certain amount of time is required from when the flow path control part executes the switching of the flow path switching part until the gas flowing into the column is replaced with a carrier gas from a column protection gas. When analysis is initiated prior to the completion of the replacement of the gas flowing into the column, the measurement precision decreases. On the other hand, waiting for the completion of the replacement of the gas for an unnecessarily long amount of time leads to the loss of time and an increase in the running cost.

By providing the configuration described above, it is possible to wait for the initiation of analysis for a sufficient amount of time required for the replacement of the gas. In addition, the length of the prescribed amount of time can be determined by measuring the amount of time required until the gas flowing into the column is replaced with the carrier gas in advance.

Alternatively, the gas chromatograph apparatus of the present invention may include:

i) a mass spectrometry apparatus into which a reference substance for mass spectrometry can be introduced; and j) a peak comparison part which, when transitioning from the standby mode to the analysis mode, performs mass spectrometry on the reference substance and the column protection gas and compares intensities of mass peaks of ions generated from the reference substance and intensities of mass peaks of ions generated from the column protection gas.

With this configuration, a certain amount of the reference substance is continuously introduced into the mass spectrometry apparatus after the flow path control part switches the flow path switching part until the transition from the standby mode to the analysis mode is completed. Whereas the intensities of the mass peaks of ions generated from the reference substance are always constant, the intensities of the mass peaks of ions generated from the column protection gas decrease as the replacement of the gas flowing into the column progresses. Accordingly, by comparing the intensities of the mass peaks of the reference substance and the intensities of the mass peaks of the column protection gas, it is possible to confirm that the gas flowing into the column has been replaced with the carrier gas.

In order to prevent the column from deteriorating during the standby mode, the column is protected by circulating the gas into the column in the gas chromatograph apparatus of the present invention in the same manner as in the prior art. However, in the gas chromatograph apparatus of the present invention, a gas that is less expensive than the carrier gas can be used as the protection gas circulated into the column in the standby mode. For example, when the carrier gas is helium gas, the column is protected in the standby state using nitrogen gas, argon gas, hydrogen gas, or the like as the column protection gas. As a result, it is possible to protect the column at a lower cost than in the conventional chromatograph apparatus which protects the column using helium gas in the standby state.

DETAILED DESCRIPTION OF THE EXEMPLARY EMBODIMENTS

Figure 1:
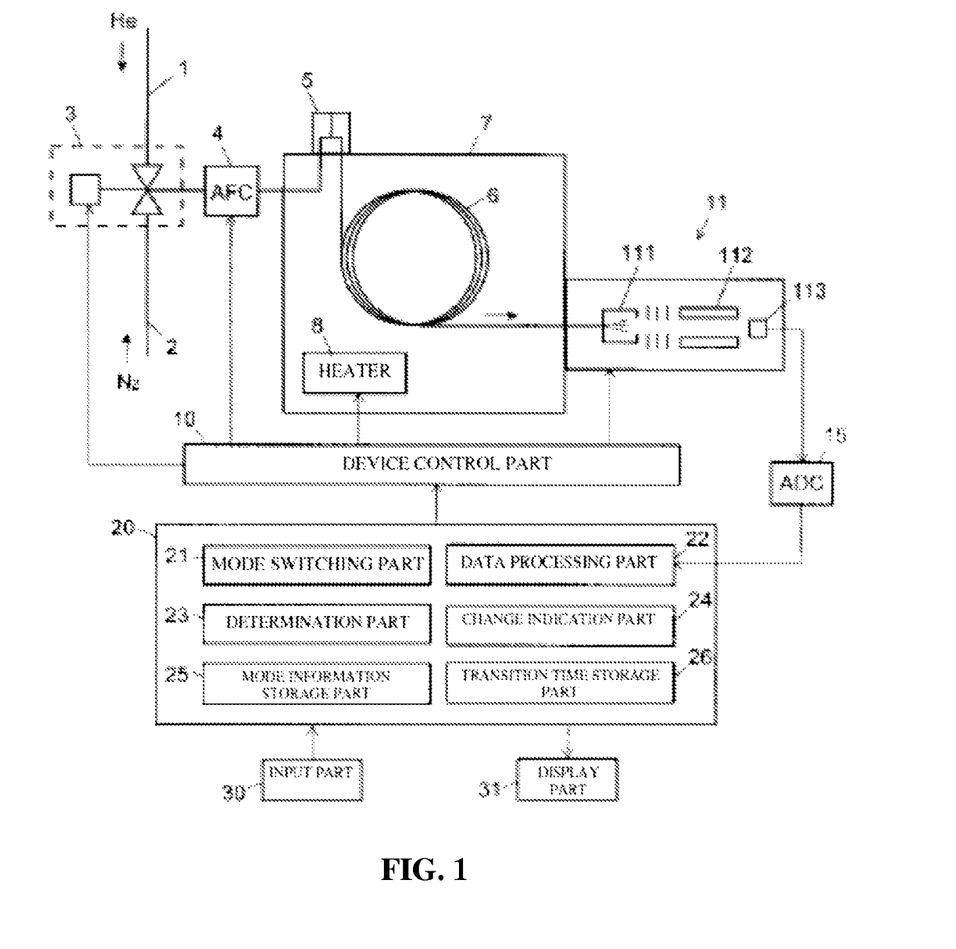
FIG. 1 is a drawing for explaining the configuration of the relevant pats of an embodiment of the gas chromatograph apparatus of the present invention.

An embodiment of the gas chromatograph apparatus of the present invention will be described hereinafter with reference to FIG. 1. The gas chromatograph apparatus of this embodiment is a GC/MS equipped with a mass spectrometry apparatus as a detection part.

The GC/MS of this embodiment includes a carrier gas flow path 1, a column protection gas flow path 2, a flow path switching part 3 for allowing only one of the aforementioned two flow paths to communicate with a flow path of a subsequent stage, a flow controller (AFC) 4 positioned at a subsequent stage following the flow path switching part 3 so as to control the flow state of the gas, a sample infusion part 5 for infusing a gas sample, a capillary column 6, and a mass spectrometry apparatus 11 disposed at the outlet end of the capillary column 6. The capillary column 6 is disposed inside a column oven 7 provided with a heater 8.

The GC/MS of this embodiment further includes a device control part 10 for operating each constituent device described above and a computer 20 for providing instructions to the device control part 10. The computer 20, which is loaded with required programs, comprises a mode switching part 21, a data processing part 22, a determination part 23, a change indication part 24, a mode information storage part 25, and a transition time storage part 26. The details of each part of the computer 20 will be described below. An input part 30 and a display part 31 are connected to the computer. 20.

First, the operation at the time of the analysis mode will be described. In the GC/MS of this embodiment, helium gas is used as the carrier gas, and nitrogen gas is used as the column protection gas. In accordance with an instruction of the mode switching part 21, the device control part 10 controls the flow path switching part 3 so as to introduce the helium gas into the capillary column 6 and infuses a gas sample from the sample infusion part 5 with a prescribed timing. The flow controller 4 executes control in the constant pressure mode so that the infusion pressure of the helium gas at the inlet end of the capillary column 6 is maintained at 100 kPa.

The respective components in the sample introduced into the capillary column 6 inside the column oven 7 via the helium gas are separated over time inside the capillary column 6 and successively reach the outlet end. Each component reaching the outlet end is ionized by an ionization part 111 of the mass spectrometry apparatus 11 and detected by an ion detector 113 after passing through a mass spectrometry part 112. After a detection signal obtained by the ion detector 113 is converted to digital by an A/D converter (ADC) 15, the signal is sent to the data processing part 22 in the computer 20.

Figure 2:
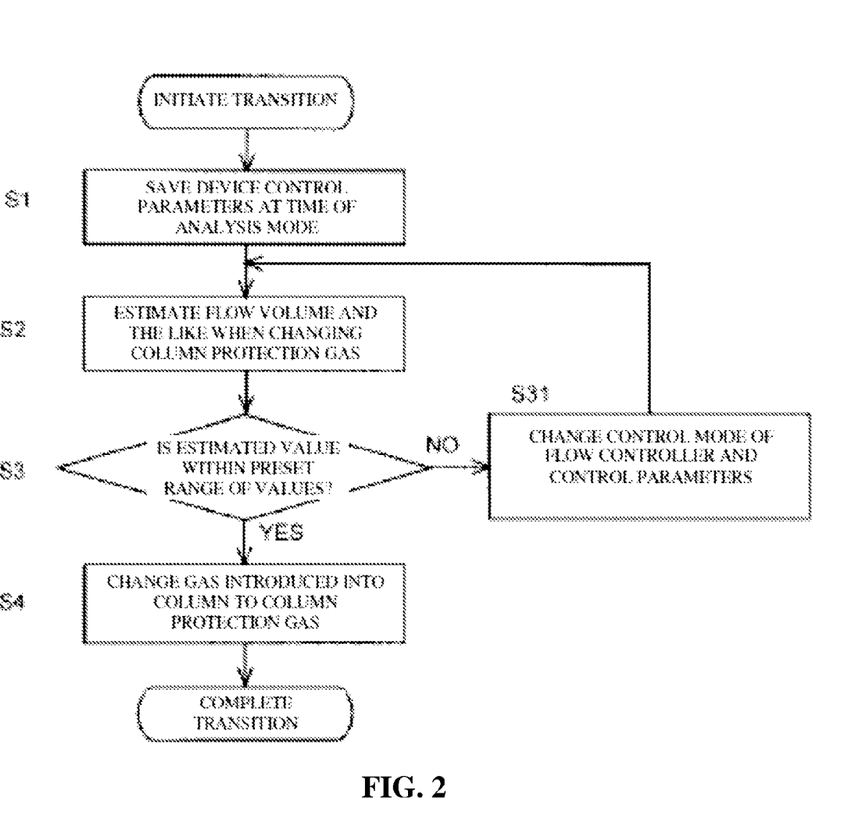
FIG. 2 is a drawing for explaining an example of the procedure for transitioning from the analysis mode to the standby mode.

Next, the transition from the analysis mode to the standby mode will be described with reference to FIG. 2. When the user indicates the transition from the analysis mode to the standby mode via the input part 30, the mode switching part 21 saves the device control parameters at the time of the analysis mode (the type of the carrier gas, the control mode of the flow controller 4, the control parameters, and the like) in the mode information storage part 25 (step S1).

The determination part 23 estimates the gas flow volume and linear velocity when the gas introduced into the column is changed from helium gas to nitrogen gas without changing the control mode (constant pressure mode) of the flow controller 4 and the control parameters (infusion pressure: 100 kPa) based on preset conditions (the viscosity of the gas, the inside diameter and length of the capillary column, the temperature of the column oven, and the like) (step S2). The determination part 23 then determines whether the estimated values are within preset ranges of values (the flow volume range that can be controlled by a gas supply device or the like, linear velocity range at which the column can be protected, and the flow volume range permitted by the mass spectrometry apparatus 11) (step S3). If an estimated value is outside the range of preset values, the determination part 23 displays a screen on the display part 31 to prompt the user to change the control mode of the flow controller 4 and/or the control parameters. When the user changes the control mode and/or the control parameters in response to this screen (step S31), the determination part 23 once again calculates and determines estimated value. This is repeated until the value estimated by the determination part 23 is within the preset range of values. Since this embodiment is a GC/MS, the "flow volume range permitted by the mass spectrometry apparatus 11" is included as one of the preset ranges of values, but this differs depending on the type of detector used.

When the setting of the control mode of the flow controller 4 and the control parameters is complete, the mode switching part 21 operates the flow path switching part 3 via the device control part 10 and changes the flow path communicating with the capillary column 6 from the carrier gas flow path 1 to the column protection gas flow path 2 (step S4). As a result, the gas introduced into the capillary column 6 is changed from helium gas to nitrogen gas, and the transition to the standby mode is complete. When the apparatus transitions to the standby mode, the gas circulating within the capillary column is gradually replaced with nitrogen gas from helium gas.

In the GC/MS of this embodiment, the capillary column can be protected by the nitrogen gas during the standby mode, so the column can be protected at a lower cost than in the conventional gas chromatograph apparatus which also circulates the helium gas during the standby mode as well.

Figure 3:
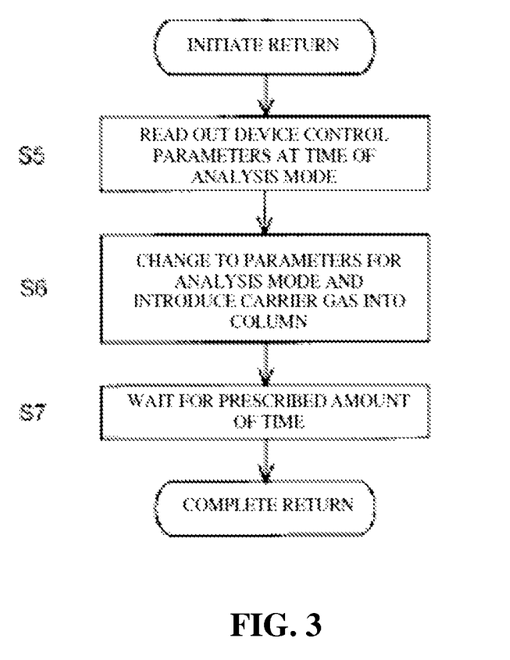
FIG. 3 is a drawing for explaining an example of the procedure for returning to the analysis mode from the standby mode.

Next, the return to the analysis mode from the standby mode will be described with reference to FIG. 3. At the point when the user attempts to end the standby mode, the nitrogen gas is circulating within the capillary column 6. Accordingly, prior to initiating the analysis of the gas sample, it is necessary to replace the nitrogen gas circulating within the capillary column 6 with helium gas used as the carrier gas.

The mode switching part 21 first reads out the device control parameters for the analysis mode from the mode information storage part 25 (step S5). The mode switching part 21 then sets the parameters of each device such as the flow controller 4 via the device control part 10 based on the device control parameters for the analysis mode that are read out. The flow path switching part 3 is then operated so as to revert the flow path communicating with the capillary column 6 to the carrier gas flow path 1 from the column protection gas flow path 2 (step S6).

Next, the mode switching part 21 reads out from the transition time storage part 26 the gas replacement time required to replace the gas inside the capillary column 6 with helium gas from nitrogen gas and waits for this amount of time (step S7). The gas replacement time is also measured by preliminary experiments and saved in the transition time storage part 26 in advance.

After the gas replacement time has elapsed, the mode switching part 21 notifies the user by displaying on the screen of the display part 31 that the gas circulating within the capillary column 6 has been replaced with helium gas and that the sample can be analyzed. In this way, the return to the analysis mode is complete.

Although the embodiment described above is a GC/MS using a mass spectrometry apparatus as a detector, the transition from the analysis mode to the standby mode and the return to the analysis mode from the standby mode can be performed with the same procedure when a detector such as a flame ionization detector (FID) or the like is used. The mode switching part 21 of this embodiment switches the mode and also functions as a flow path control part and a notification part.

Next, another embodiment will be described with reference to FIGS. 4 and 5, wherein in the return to the analysis mode from the standby mode, the return to the analysis mode is thus completed by confirming that the gas inside the capillary column has been replaced with helium gas from nitrogen gas by means of a different method.

Figure 4:
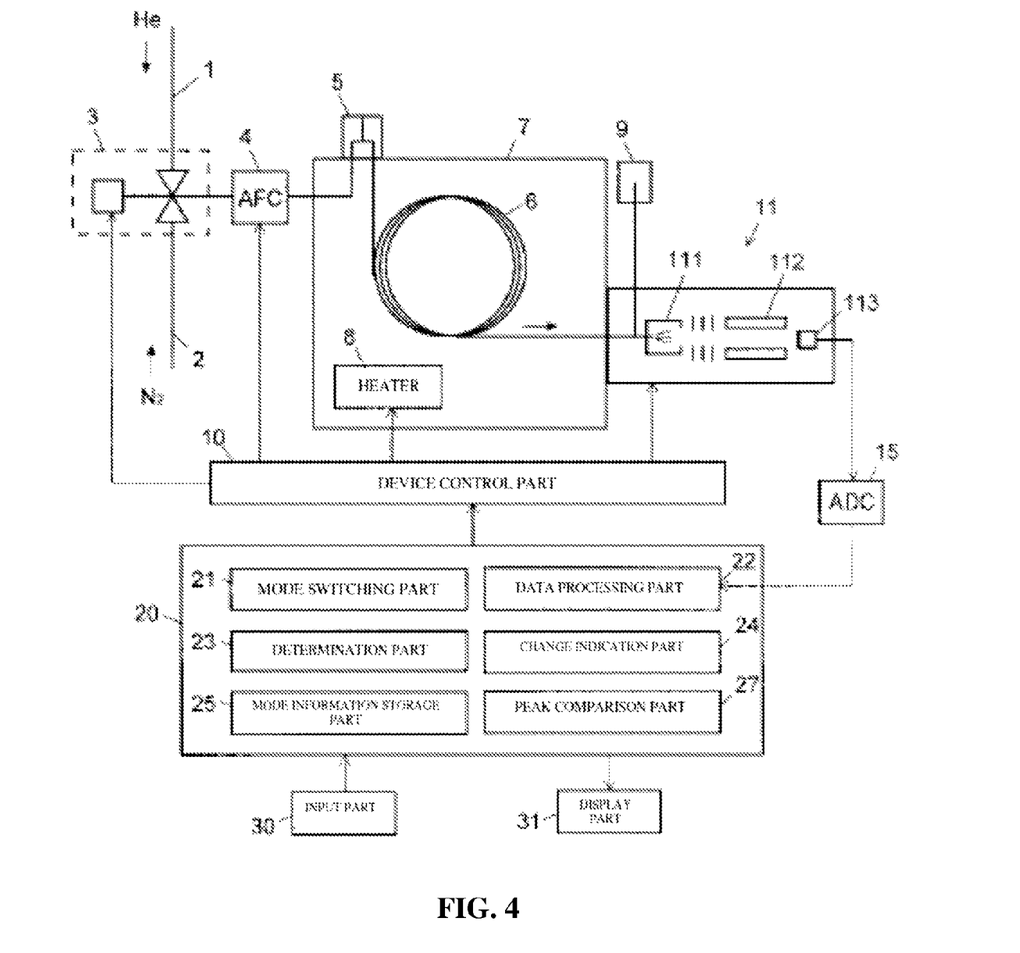
FIG. 4 is a drawing for explaining the configuration of the relevant parts of another embodiment of the gas chromatograph apparatus of the present invention.
Figure 5:
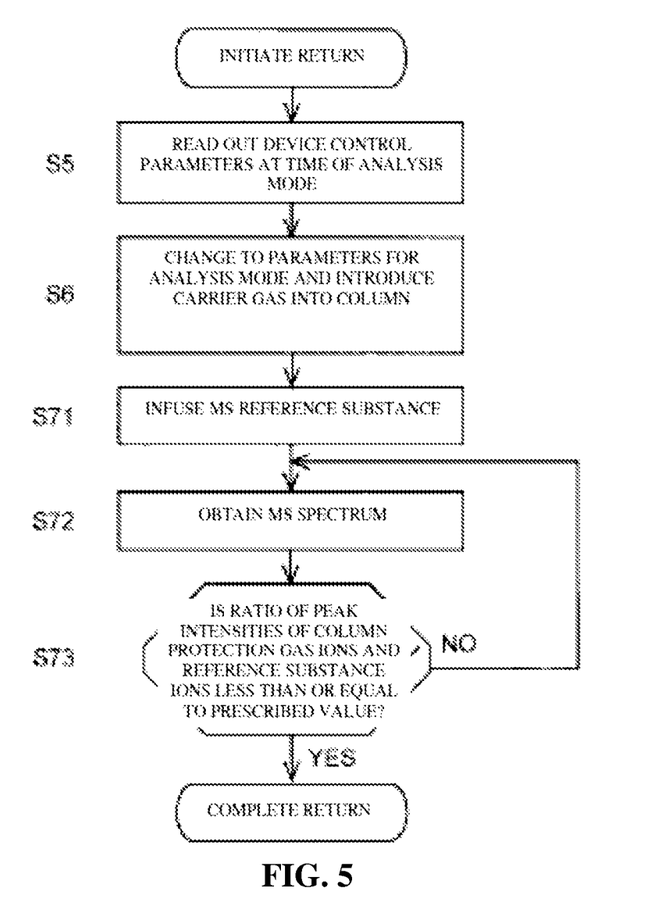
FIG. 5 is a drawing for explaining another example of the procedure for returning to the analysis mode from the standby mode.

The apparatus configuration in this case is illustrated in FIG. 4. This GC/MS is equipped with a reference substance infusion part 9 for infusion PFTBA as a reference substance used in mass spectrometry at a position in front of the ionization part 111. The computer 20 also has a peak comparison part 27 for performing operations described below. Since the configuration is otherwise the same as in the GC/MS illustrated in FIG. 1, all other components are labeled with the same symbols and will not be explained. In addition, since parts of the standby mode transition steps (step S1 to step S4) and the analysis mode returning steps (step S5 and step S6) in this embodiment are the same as in the embodiment described above, these will not be explained here.

In the configuration illustrated in FIG. 4, after step S6 described above is performed, the reference substance infusion part 9 continues to infuse a constant volume of PFTBA in accordance with the instruction of the mode switching part 21 (step S71). As a result, PFTBA is introduced into the ionization part 111 of the mass spectrometry apparatus in addition to the nitrogen gas and helium gas, and the respective gases are ionized. After these ions pass through the mass spectrometry part 112, the ions are detected by the ion detector 113. After a detection signal obtained by the ion detector 113 is A/D-converted by the A/D converter 15, the signal is spectralized by the data processing part 22 and displayed on the display part 31 (step S72).

At this time, the peak comparison part 27 compares the intensities of ions generated from respective nitrogen gas and PFTBA (step S73). At the point when the ratio of these peak intensities falls below a preset value, it is assessed that the gas flowing into the capillary column 6 has been replaced with the helium gas from the nitrogen gas.

In response to this, the mode switching part 21 notifies the user by displaying on the screen of the display part 31 that the sample can be analyzed. PFTBA in this embodiment is given as an example of the reference substance used in mass spectrometry, and the type of the reference substance is not, of course, limited to this example.

Both of the embodiments described above are examples and can be modified or corrected appropriately in accordance with the gist of the present invention.

For example, in the embodiments described above, cases in which the carrier gas was helium gas and the column protection gas was nitrogen gas were explained as examples, but the present invention is not limited to this combination and may incorporate a combination in which the column protection gas is a gas that is less expensive than the carrier gas. In this case, it is not absolutely necessary to make the column protection gas a gas of a different type than the carrier gas, and a gas of the same type as the carrier gas but with a lower purity may also be used.

In addition, even with a comparatively expensive gas, there are cases in which the column can be protected at a low cost by suppressing the flow volume of the gas circulated into the column based on the characteristics of the column that is used or the viscosity of the gas in question. An example of this is illustrated in FIG. 6.

Figure 6:
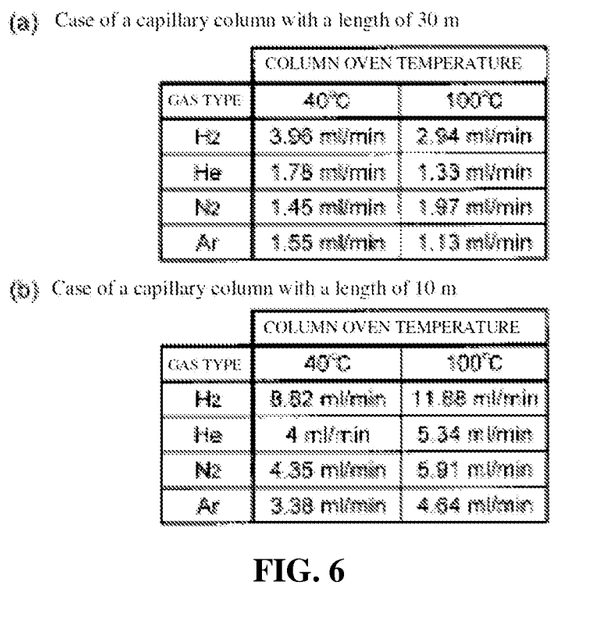
FIG. 6 is a drawing for explaining the results of the calculation of the gas flow volume when controlling the flow state in the constant pressure mode.

FIG. 6 shows the results of calculating the flow volumes of various gases (hydrogen gas, helium gas, nitrogen gas, and argon gas) when the flow controller controls the flow state of the gas in the constant pressure mode (infusion port pressure: 100 kPa) and introduces the gas into a capillary column with an inside diameter of 0.25 mm in the GC/MS apparatus. FIG. 6 (a) shows the results for the case of a capillary column with a length of 30 m, and FIG. 6 (b) shows the results for the case of a capillary column with a length of 10 m, wherein the results of performing calculations in the cases in which the temperature of the capillary column is 40° C. and 100° C., respectively, are shown. When argon gas is used under these conditions, although the gas itself is comparatively expensive, the column can be protected at a low cost by suppressing the flow volume.

In the embodiments described above, examples in which the flow controller 4 controls the flow state of the gas in the constant pressure mode were described, but the flow controller 4 may also control the flow state of the gas in the constant flow volume mode or the constant linear velocity mode. In this case, the determination part 23 calculates estimated values for values other than the parameters controlled by constant values and determines whether the values are within prescribed ranges of values.

In addition, the apparatus may be configured that the device control parameters at the time of a plurality of analysis modes (the types of carrier gasses, the control modes of the flow controller 4, the control parameters, and the like) and the device control parameters at a plurality of standby modes are saved in the mode information storage part 25 as method files in advance, and the user selects a desired mode from among these modes via the input part 30 so as to make the mode switching part 21 execute a switch in the mode (transition from the analysis mode to the standby mode and return to the analysis mode from the standby mode). As a result, it becomes unnecessary for the determination part 23 to make estimations or determinations each time the mode transitions from the analysis mode to the standby mode, which increases the efficiency of mode switching. Moreover, in this case, it is possible to return to an analysis mode of different device parameters than the previous analysis mode when returning to the analysis mode from the standby mode.

In addition, all of the embodiments described above were described using a gas chromatograph apparatus using a capillary column as an example, but the present invention can also be applied to a gas chromatograph apparatus using a packed column.

EXPLANATION OF REFERENCES

1 . . . carrier gas flow path
2 . . . column protection gas flow path
3 . . . flow path switching part
4 . . . flow controller
5 . . . sample infusion part
6 . . . capillary column
7 . . . column oven
8 . . . heater
9 . . . reference substance infusion part
10 . . . device control part
11 . . . mass spectrometry apparatus
20 . . . computer
21 . . . mode switching part
22 . . . data processing part
23 . . . determination part
24 . . . change indication part
25 . . . mode information storage part
26 . . . transition time storage part
27 . . . peak comparison part
30 . . . input part
31 . . . display part
111 . . . ionization part
112 . . . mass spectrometry part
113 . . . ion detector

What is claimed is:

1. A gas chromatograph apparatus having a column which separates respective components contained in a gas sample introduced via a carrier gas over time, wherein an analysis mode in which an analysis of said gas sample is executed and a standby mode in which an analysis is not executed can be switched and executed, said gas chromatograph apparatus comprising:

a) a carrier gas flow path for introducing said carrier gas into said column;

b) a column protection gas flow path for introducing a column protection gas separate from said carrier gas into said column;

c) a flow path switching part provided between said carrier gas flow path and said column protection gas flow path and said column so that only one of said carrier gas or said column protection gas is introduced into the column;

d) a flow path control part for introducing said carrier gas into said column at the time of said analysis mode and introducing said column protection gas into said column at the time of said standby mode;

e) a flow controller having at least one control mode from among a constant linear velocity mode, a constant flow volume mode, and a constant pressure mode as a mode for controlling a flow state of a gas introduced into said column;

f) a determination part for estimating at least one value of a linear velocity, a flow volume of the column protection gas, and a pressure of the column protection gas when the gas introduced into said column is changed from said carrier gas to said column protection gas without changing the control mode of said flow controller and parameters related to said mode at the time of a transition from said analysis mode to said standby mode and determining whether the estimated value is within a preset range; and g) a change indication part for prompting a user to change the control mode of said flow controller and/or the parameters related to said mode by means of a predetermined method if said determination part determines that said estimated value is not within said range.

2. The gas chromatograph apparatus according to claim 1, comprising:

h) a notification part for notifying a user that the replacement of the column protection gas with the carrier gas has been completed by means of a prescribed method after a prescribed amount of time has passed since the switching performed by said flow path switching part at the time of a transition from said standby mode to said analysis mode.

3. The gas chromatograph apparatus according to claim 1, comprising:

i) a mass spectrometry apparatus into which a reference substance for mass spectrometry can be introduced; and j) a peak comparison part which, when transitioning from said standby mode to said analysis mode, performs mass spectrometry on said reference substance and said column protection gas and compares intensities of mass peaks of ions generated from said reference substance and intensities of mass peaks of ions generated from said column protection gas.

4. The gas chromatography apparatus according to claim 1, wherein the carrier gas is helium and the column protection gas is nitrogen.

5. A method for protecting a column in a gas chromatograph which separates respective components contained in a gas sample introduced via a carrier gas over time, wherein an analysis mode in which an analysis of said gas sample is executed and a standby mode in which an analysis is not executed can be switched and executed, said gas chromatograph comprising a flow controller having at least one control mode from among a constant linear velocity mode, a constant flow volume mode, and a constant pressure mode as a mode for controlling a flow state of a gas introduced into said column, the method comprising:

receiving an instruction from a user regarding a selected mode;

introducing said carrier gas in a carrier gas flow path in response to said analysis mode being selected by the user; and introducing a column protection gas separate from said carrier gas in response to said standby mode being selected by the user;

switching between only said carrier gas and only said column protection gas in response to the instruction of the user so that only one of said carrier gas or said column protection gas is introduced into the column by a flow path switching part provided between said carrier gas flow path and said column protection gas flow path and said column;

estimating at least one value of a linear velocity, a flow volume of the column protection gas, and a pressure of the column protection gas when the gas introduced into said column is changed from said carrier gas to said column protection gas without changing the control mode of said flow controller and parameters related to said mode at the time of a transition from said analysis mode to said standby mode and determining whether the estimated value is within a preset range; and prompting the user to change the control mode of said flow controller and/or the parameters related to said mode by means of a predetermined method if it is determined that said estimated value is not within said range.

6. The method according to claim 5, wherein the carrier gas is helium and the column protection gas is nitrogen.

* * * * *